United States Patent [19]

Bodley et al.

[11] Patent Number: 5,679,660
[45] Date of Patent: Oct. 21, 1997

[54] PHARMACEUTICAL COMPOSITION COMPRISING DICLOFENAC AND CYCLODEXTRIN

[75] Inventors: Mark David Bodley, Charlo; Lueta Ann Glintenkamp, The Barn; Lawrence John Penkler, Lorraine; Michiel Coenraad Bosch van Oudtshoorn, Monument Park, all of South Africa

[73] Assignee: Farmarc Nederland BV, Amsterdam, Netherlands

[21] Appl. No.: 352,866

[22] Filed: Dec. 2, 1994

[30] Foreign Application Priority Data

Dec. 2, 1993 [ZA] South Africa ............................ 93/9031

[51] Int. Cl.$^6$ ...................... A61K 31/715; A61K 31/135
[52] U.S. Cl. .............................. 514/58; 514/658; 514/886
[58] Field of Search ............................... 514/58, 658, 886

[56] References Cited

U.S. PATENT DOCUMENTS 4,983,586  1/1991  Bodor ......................................... 514/58

FOREIGN PATENT DOCUMENTS

| 0 335 545 | 10/1989 | European Pat. Off. . |
| 0519428 | 12/1992 | European Pat. Off. . |
| 4207922 | 9/1993 | Germany . |
| 6-016547 | 1/1994 | Japan . |
| 9002141 | 3/1990 | WIPO . |
| 92/00725 | 1/1992 | WIPO . |

OTHER PUBLICATIONS

*Journal of Pharmaceutical Sciences*, vol. 83, No. 9, Sep. 1994, "In Vitro Corneal Permeability of Diclofenac Sodium in Formulations Containing Cyclodextrins Compared to the Commercial Product Voltraren Ophtha", Olaf Reer et al., pp. 1345–1349.

*Elsevier Science Publishers B.V. (Biomedical Division)*, 1987, "Cyclodextrin Inclusion Compounds: Effects on Stability and Bio–Pharmaceutical Properties", K. Uekama, pp. 181–193.

T. Backensfeld et al., "Interaction of NSA with Cyclodextrins and Hydroxypropyl Cyclodextrin Derivatives", Int. J. Pharm. 1991, 74, pp. 85–93.

T. Backensfeld et al., "Solubilization and Stabilization of Non–Steroidal Antirheumatics with Cyclodextrins and Cyclodextrin Ethers", Arch. Pharm. 323, p. 690, 1990.

I. Orienti et al, "Inclusion Complexes Between Non Steroidal Antiinflammatory Drugs and β–Cyclodextrin", Dur. J. Pharm. Biopharm. 37, 1991 pp. 110–112.

I. Orienti et al., "Availability of nsiadh β–Cyclodextrin Inclusion Complexes", Arch. Pharm. (Weinheim) 322, 1989, pp. 207–211.

English Abstract of Russian Article, "Preparing the Inclusion Compounds Orthophen and Indomethcin with β–Cyclodextrin and their Derivatographic Analysis," Nekroshus, ES et al., Farmatsiya Moscow, 1989, 38, pp. 29–34.

S. Devi et al,. "Albumin Microspheres and β–Cyclodextrin Inclusion Complex Containing Diclofenac Sodium" Ind. J. Pharm. Sci, 54, 1992, pp. 259–261.

M. Kurozumi et al., "Inclusion Compounds of Non–Steroidal Antiinflammatory and Other Slightly Water Soluble Drugs with α– and β–Cyclodextrins in Powdered Form," Chem. Pharm. Bull. 23, 1975, pp. 3062–3068.

English Abstract of Japanese Patent Application No. 59–084821 to Teikoku Chemical Industries Limited, 1984.

English Abstract of Japanese Patent Application No. 60–16540 to Wakamoto Pharm. Co., Ltd., 1985.

M. Otagiri et al., "Comparative Study on Inclusion Complexation of β–Cyclodextrin and Tri–O–Methyl–β–Cyclodextrin with Several Drugs in Aqueous Solution", Acta Pharm. Suec. 21, pp. 357–366, 1984.

K. Ikeda et al., "Inclusion Complexes of β–Cyclodextrin with Antiinflammatory Drugs Fenamates in Aqueous Solution", Chem. Pharm. Bull. vol. 23 (1), 1975, pp. 201–208.

English Abstract(s) of JP–A–60–16547 to Wakamoto Pharm. Co., Ltd., 1994.

*Primary Examiner*—Kathleen K. Fonda
*Attorney, Agent, or Firm*—Cushman Darby & Cushman Intellectual Property Group of Pillsbury Madison & Sutro LLP

[57] ABSTRACT

A method of preparing an injectable pharmaceutical or veterinary composition which comprises either diclofenac or a salt thereof and 2-hydroxypropyl beta-cyclodextrin, or an inclusion complex of diclofenac or a salt thereof and 2-hydroxypropyl beta-cyclodextrin, includes the step of dissolving either the diclofenac or salt thereof and the 2-hydroxypropyl beta-cyclodextrin, or the inclusion complex, in water to form a solution, the water having been acidified to a pH such that the pH of the solution is from 6.0 to 8.5 inclusive, in the absence of a phosphate buffer. The composition so produced has good stability on storage.

13 Claims, 7 Drawing Sheets

R = CH₂CHOHCH₃

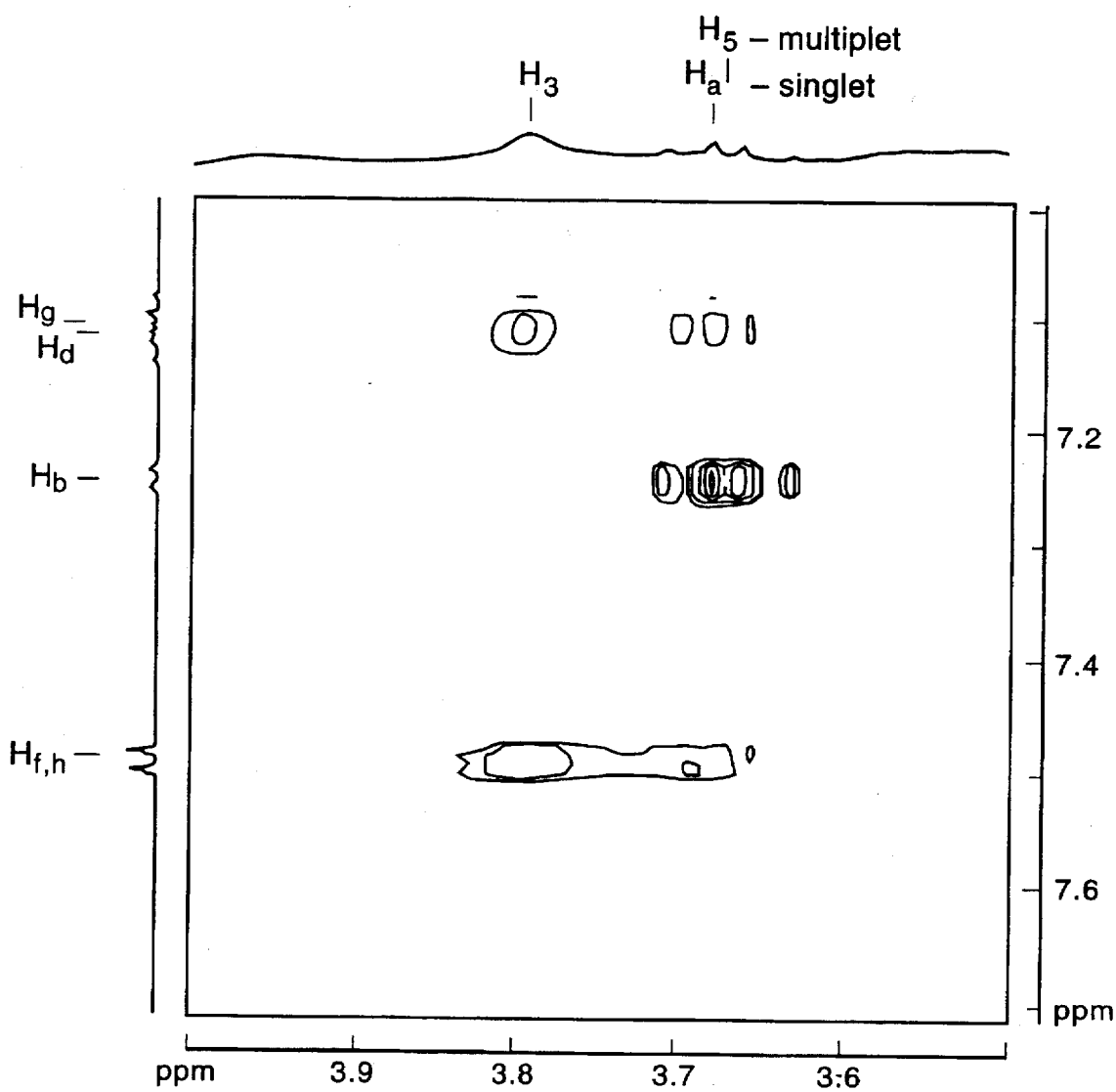

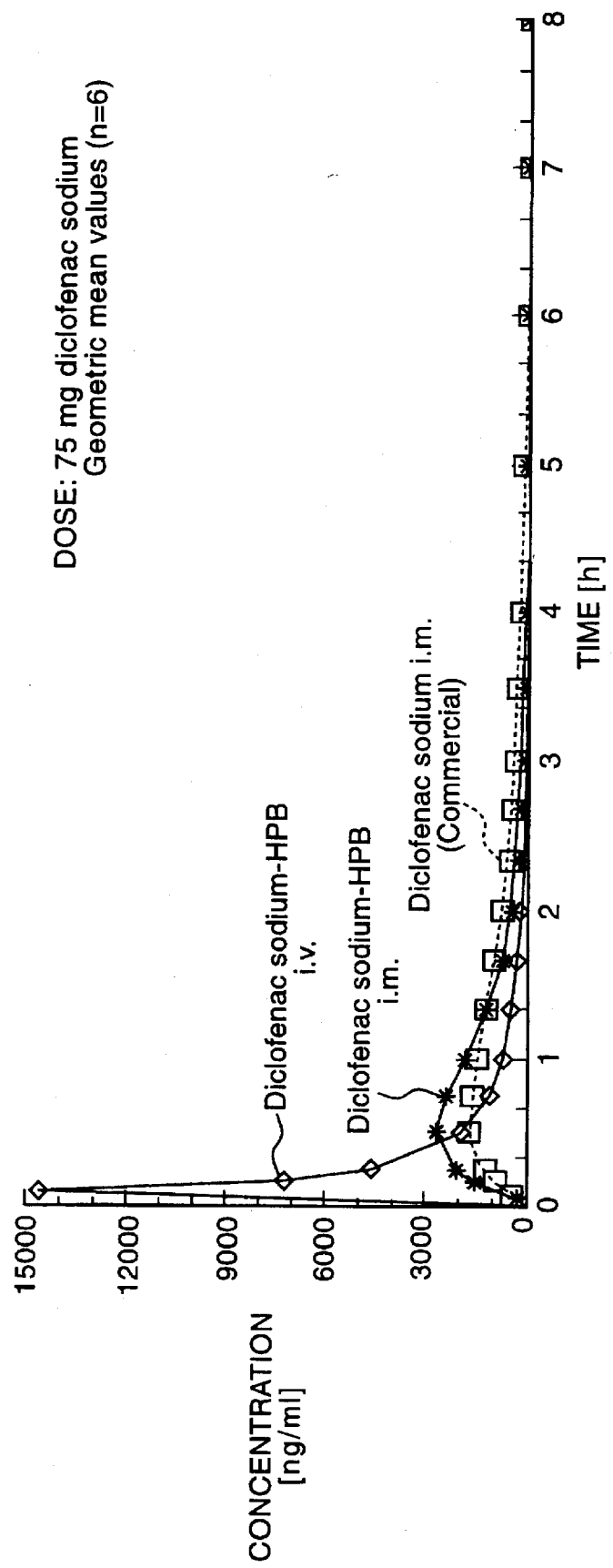

PHARMACEUTICAL COMPOSITION COMPRISING DICLOFENAC AND CYCLODEXTRIN

BACKGROUND OF THE INVENTION

This invention relates to a method of preparing an injectable pharmaceutical or veterinary composition comprising either diclofenac or a pharmaceutically acceptable salt thereof and 2-hydroxypropyl beta-cyclodextrin, or an inclusion complex of diclofenac or a pharmaceutically acceptable salt of diclofenac and 2-hydroxypropyl beta-cyclodextrin, and to an injectable composition so formed.

Diclofenac is a non-steroidal anti-inflammatory drug which inhibits the synthesis of prostaglandins by acetylation of the enzyme cyclo-oxygenase. Prostaglandins that are released by trauma and various other stimuli do not cause pain directly but cause hyperalgesia by increasing the sensitivity of nerve endings to the effects of pain-producing substances.

In order for a drug to achieve maximal relief of acute pain or prevent post-operative pain, the drug should reach the systemic circulation as soon as possible after administration. This is achieved by intravenous administration.

Further, in certain circumstances, oral administration of drugs is not possible or desirable. For example, acute painful conditions, e.g. migraine, trauma, dysmenorrhoea and renal or biliary colic are often accompanied by nausea and vomiting, rendering the oral route of administration ineffective. Gastric emptying may also be delayed under these conditions. Further, surgical patients are usually fasted during the peri-operative period and the parenteral route is indicated for administration of analgesic drugs at this time.

There is thus a need for an injectable composition containing diclofenac or a pharmaceutically acceptable salt thereof for the treatment of both acute painful conditions and post-operative patients.

However, the solubility of diclofenac and its sodium salt are very limited in aqueous solutions around physiological pH. Parenteral or injectable formulations of diclofenac or diclofenac sodium have therefore necessitated the use of solubilizing additives such as propylene glycol. Commercial formulations suffer from a strict limitation to deep intramuscular injection.

In a paper in International Journal of Pharmaceutics, 74 (1991) 85–93, entitled "Interaction of NSA with cyclodextrins and hydroxypropyl cyclodextrin derivatives" by Backensfeld, Müller and Kolter, there is disclosed a study to increase the aqueous solubility and stability of the NSA indomethacin, diclofenac and piroxicam with hydroxyalkylated cyclodextrin derivatives. Diclofenac solutions with and without oxygen were prepared for the stability tests of diclofenac. The solutions were prepared by mixing diclofenac sodium ($6.3 \times 10^{-3}$M which corresponds to 2.0 mg diclofenac sodium per milliliter) with phosphate buffer, pH 7.4 Ph. Eur. and was dissolved in double the quantity ($12.6 \times 10^{-3}$M) of beta-cyclodextrin (β-CD) or hydroxypropyl beta-cyclodextrin (HP-β-CD) MS 0.39 which is equivalent to an average degree of substitution (DS) OF 2.73 hydroxypropyl groups per cyclodextrin molecule. Each batch was filtered through a 0.22 μm membrane filter and filled into sterile 5 ml glass ampoules. Although the study concluded that the CD derivative had the most stabilizing effect on diclofenac solutions, it was also found that the solutions lacking additive proved to be physically unstable due to the precipitation of crystalline diclofenac observed during a short storage time. This would render the solutions unfit for the preparation of injectable compositions.

The following further prior art is known in relation to inclusion complexes of cyclodextrins and diclofenac.

(1) Beta-cyclodextrin and particularly hydroxyalkyl ether derivatives have been reported to increase the aqueous solubility of diclofenac [Solubilization and Stabilization of Non-Steroidal Antirheumatics with Cyclodextrins and Cyclodextrin Ethers, Backensfeld, T. and Mueller, B. W. Arch. Pharm. 1990, 323, 690]

(2) The interaction of diclofenac with beta-cyclodextrin as a function of temperature and pH has been reported [Inclusion Complexes between Non Steroidal Antiinflammatory Drugs and β-Cyclodextrin, Orienti, I., Fini, A., Bertasi, V. and Zecchi, V. Eur. J. Pharm. Biopharm. 1991, 37, 110–112].

The above studies (1 and 2) rely on phase solubility analysis which involves the determination of the effect of increasing concentrations of cyclodextrin on the solubility of excess diclofenac sodium under a variety of conditions. There is no mention of the preparation or isolation of a solid inclusion complex.

(3) The diffusability of a diclofenac (acid) complex with beta cyclodextrin has been reported [Availability of NSAIDH β-Cyclodextrin Inclusion Complexes, Orienti, I., Cavallari, C. and Zecchi, V. Arch. Pharm (Weinheim) 1989, 322, 207–211]. The complex was prepared according to a previously described coprecipitation method involving addition of the drug, dissolved in ethyl ether, to a solution of cyclodextrin in water, agitating for 24 hours, cooling, isolating product, washing with ethyl ether and drying. The complex was not characterized and stoichiometry was only assumed to be 1:1.

(4) An inclusion complex of diclofenac sodium and beta-cyclodextrin has been prepared by concurrent crystallization from water-organic systems. [Preparing the inclusion compounds orthophen and indomethacin with beta-cyclodextrin and their derivatographic analysis, Nekroshus, E. S. and Reshetnyak, V. Y. Farmatsiya Moscow 1989, 38, 29–34]. The findings of derivatographic analysis and thin layer chromatography provide support of drug-cyclodextrin inclusion at a molar ratio of 1:2.

(5) An inclusion complex of diclofenac sodium and beta cyclodextrin was formulated as microspheres using crosslinked egg albumin and hydroxypropylmethylcellose [Albumin Microspheres and Beta-cyclodextrin Inclusion Complex Containing Diclofenac Sodium, Devi, S. G et al. Ind. J. Pharm. Sci. 1992, 54, 259–261]. Relative to free diclofenac sodium poor overall release was obtained for the complex as measured by diffusion of the drug across dialysis membrane. Details of preparation of the complex are not described and neither are any analytical methods described to provide evidence of complexation.

In the above studies (3 and 4) the so-called co-precipitation method of complex formation is described. The co-precipitation method is known generally to produce low yields of complex [Inclusion Compounds of Non-Steroidal Antiinflammatory and other slightly water soluble drugs with α- and β-Cyclodextrins in Powdered Form; Kurozumi, M. et al. Chem. Pharm. Bull. 1975, 23, 3062–3068].

(6) PCT WO90/02141 to Australian Commercial Research and Development Limited teaches inclusion complexes comprising an amino cyclodextrin derivative wherein at least one C2, C3 or C6 hydroxyl is substituted with $NH_2$, and inclusion complexes comprising a cyclodextrin having at least one substitution where a C2, C3 or C6 hydroxyl is substituted with a group selected from a particular list, the active component of the complex being for example diclofenac. In addition this reference covers a pharmaceutical composition for oral administration containing such an inclusion complex.

(7) European Patent Application No 519428 to Takeda Chemical Industries Limited teaches a pharmaceutical composition comprising a slightly water soluble drug, for example diclofenac, a cyclodextrin and a water soluble organic solvent, particularly for injection. It is mentioned that in many cases the composition forms an inclusion compound with the cyclodextrin. It is also mentioned that the cyclodextrin may be beta-cyclodextrin.

(8) Japanese Patent Application No JP59084821 to Teikoku Chemical Industries Limited teaches a sustained release preparation of diclofenac which contains cyclodextrin. The molar ratio of cyclodextrin to diclofenac is 0.05–1.0. Alpha-cyclodextrin, beta-cyclodextrin or gamma-cyclodextrin may be used. In the preparation of this product, diclofenac is mixed with cyclodextrin. After the addition of water, the mixture is kneaded and dried. Alternatively, diclofenac and cyclodextrin are added to water and stirred well. After filtration, the filtrate is spray dried or lyophilised.

(9) Japanese Patent Application No JP6016547 to Wakamoto Pharmaceutical Company Limited teaches an antiphlogistic eyedrop which comprises a diclofenac sodium salt and at least one water soluble cyclodextrin, being a substituted cyclodextrin.

(10) German Patent Application No 4207922 to Pharmatech GmbH teaches water soluble inclusion complexes of diclofenac sodium and either methyl-beta-cyclodextrin with a degree of substitution of 0.4, methyl-beta-cyclodextrin with a degree of substitution of 0.6 or hydroxypropyl-beta-cyclodextrin with a degree of substitution of 0.42 per glucose unit which is equivalent to an average degree of substitution of 2.94 hydroxypropyl groups per cyclodextrin molecule.

SUMMARY OF THE INVENTION

According to a first aspect of the invention there is provided a method of preparing an injectable pharmaceutical or veterinary composition comprising either (a) diclofenac or a pharmaceutically acceptable salt thereof and 2-hydroxypropyl beta-cyclodextrin or (b) an inclusion complex of diclofenac or a pharmaceutically acceptable salt of diclofenac and 2-hydroxypropyl beta-cyclodextrin, or a mixture of (a) and (b), which includes the step of:

(i) dissolving either (a) diclofenac or a pharmaceutically acceptable salt thereof and 2-hydroxypropyl beta-cyclodextrin, or (b) an inclusion complex of diclofenac or a pharmaceutically acceptable salt of diclofenac and 2-hydroxypropyl beta-cyclodextrin, or a mixture of (a) and (b), in water to form a solution, the water having been acidified to a pH such that the pH of the solution is from 6.0 to 8.5 inclusive, in the absence of a phosphate buffer.

By a "pharmaceutically acceptable" salt or agent there is meant a salt or agent which is acceptable for human or veterinary use.

It has been found that by preparing the solution in the absence of a phosphate buffer and preferably also with little or no sodium ions present, there is produced a solution from which the diclofenac or salt thereof does not crystallize out and therefore which is suitable for use as an injectable composition.

The method of the invention may include any one or more of the following additional steps:

(ii) adjusting the osmolality of the solution by adding a pharmaceutically acceptable organic osmolality modifying agent such as for example mannitol, dextrose or sorbitol;
(iii) degassing the solution with nitrogen;
(iv) sterilizing the solution by filtration;
(v) filling the solution into ampoules or vials; or
(vi) freeze-drying the solution to provide a lyophilized product for reconstitution.

When the composition contains a mixture of diclofenac or a pharmaceutically acceptable salt thereof and 2-hydroxypropyl beta-cyclodextrin (option (a)) then the molar ratio of the two is preferably 1:1 to 1:10, more preferably 1:1.5 to 1:2.5.

An inclusion complex of diclofenac or a pharmaceutically acceptable salt thereof and hydroxypropyl beta-cyclodextrin may be prepared by mixing together with kneading or grinding or the like an amount of diclofenac or a pharmaceutically acceptable salt thereof and an amount of 2-hydroxypropyl beta-cyclodextrin, in a molar ratio of 1:1 to 1:10, preferably 1:1.5 to 1:2.5.

The mixing is preferably carried out in the presence of a small amount of water or an aqueous alcoholic solution.

The average degree of substitution of the 2-hydroxypropyl beta-cyclodextrin is preferably between 3.9 and 5.1 2-hydroxypropyl groups per cyclodextrin molecule.

According to a second aspect of the invention there is provided an injectable pharmaceutical or veterinary composition comprising either (a) diclofenac or a pharmaceutically acceptable salt thereof and 2-hydroxypropyl beta-cyclodextrin, or (b) an inclusion complex of diclofenac or a pharmaceutically acceptable salt of diclofenac and 2-hydroxypropyl beta-cyclodextrin, or a mixture of (a) and (b), in an aqueous vehicle in the form of a solution or adapted to be reconstituted with an aqueous vehicle to give a solution, the solution having a pH of from 6.0 to 8.5 inclusive, the solution being free of any phosphate buffer.

The composition preferably has a concentration of diclofenac of 10 mg per milliliter or more, preferably about 25 mg per milliliter.

The composition may be formulated in unit dose form, each unit dose containing from 10 mg to 150 mg inclusive of diclofenac.

BRIEF DESCRIPTION OF THE DRAWINGS

FIG. 5 is a section of 2-D ROESY spectrum of the complex of diclofenac sodium and 2-hydroxypropyl beta-cyclodextrin in $D_2O$ solution showing through space correlations between protons of diclofenac sodium and 2-hydroxypropyl beta-cyclodextrin;

FIG. 7 is a graph of the mean plasma diclofenac concentration versus time curves of commercial diclofenac sodium (i.m.) and diclofenac sodium - HPB (i.m.) and (i.v.) after cross-over administration to six normal human volunteers.

DESCRIPTION OF EMBODIMENTS

Figure 1:
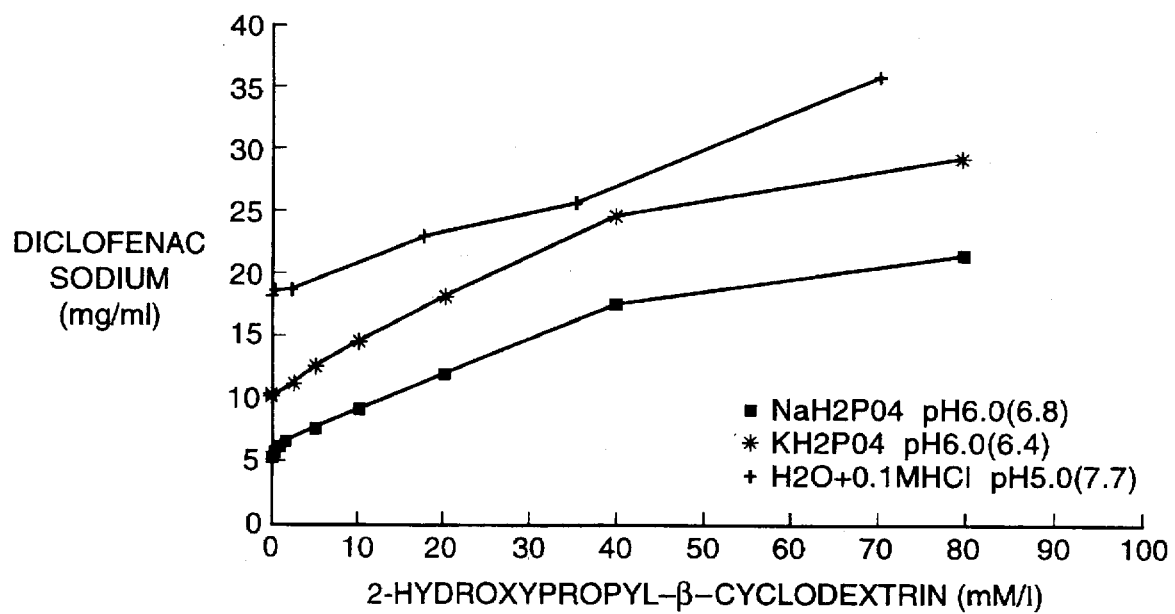
FIG. 1 is a graph showing the effect of increasing concentration of 2-hydroxypropyl beta-cyclodextrin on diclofenac sodium solubility in aqueous solution at 25° C. and various pH values.

The invention relates to a method of preparing an injectable pharmaceutical or veterinary composition comprising either (a) diclofenac (I) or a pharmaceutically acceptable salt thereof such as diclofenac sodium (II) and 2-hydroxypropyl beta-cyclodextrin (III) or (b) an inclusion complex of (I) or a pharmaceutically acceptable salt of (I) such as (II), and (III), or a mixture of (a) and (b).

The major step of the method is to dissolve either I or a salt thereof such as II, and III, or an inclusion complex of I or a salt thereof such as II, and III, or a mixture thereof, in water to form a solution, the water having previously been acidified to a pH such that the pH of the solution is from 6.0 to 8.5 inclusive, in the absence of a phosphate buffer.

When the composition contains a mixture of I or II, and III, then the molar ratio of I or II to III is preferably 1:1 to 1:10, more preferably 1:1.5 to 1:2.5.

The molar mass of III is calculated from the average degree of substitution (D.S.) by the formula:

$$MW = (1135 - D.S.) + (D.S. \times 59)$$

A solid inclusion complex of I or a salt thereof such as II, in III may be prepared by vigorous kneading or grinding of the solids in the presence of a small amount of water or aqueous alcoholic solution. The molar ratio of I or II to III may be varied between 1:1 to 1:10. A preferred ratio is between 1:1.5 and 1:2.5. The mixing process is preferably carried out for about 30 to 60 minutes, after which the product is preferably dried in an oven at about 40° C. The product obtained is reground, passed through a 60 mesh screen and homogenized. The product is characterized by a fine particle size and good water solubility. It consists of a I/III or II/III molecular inclusion complex as demonstrated by IR spectroscopy and DSC (differential scanning calorimetry) analysis.

Preferably, I or II, and III, or the solid inclusion complex of I/III or II/III or mixtures thereof are dissolved in warm water previously acidified with 0,1N hydrochloric acid to an empirically determined pH such that the pH of the resulting solution is between 6.0 and 8.5. This must be done in the absence of a phosphate buffer and preferably in a solution which contains little or no sodium or potassium ions.

If desired, the osmolality of the solution may be adjusted by adding a pharmaceutically acceptable organic osmolality modifying agent such as mannitol, dextrose or sorbitol.

The solution may contain other physiologically compatible compounds such as potassium nitrate, sodium metabisulphite, benzalkonium chloride, chlorobutanol, xylitol or glucose.

The finished solution is preferably degassed with nitrogen and sterilized by filtration. Thereafter, the solution may be aseptically transferred into vials or ampoules under nitrogen atmosphere. Alternatively, the solution may be freeze dried to provide a lyophilized product for reconstitution.

The injectable composition of the invention preferably has a concentration of I of 10 mg per milliliter, more preferably about 25 mg per milliliter.

The injectable composition of the invention may be formulated in unit dose form, each unit dose containing from 10 mg to 150 mg inclusive of I.

The injectable composition produced by the method of the invention may be used in the treatment of acute painful inflammatory conditions in humans and animals such as migraine, trauma, dysmenorrhoea, renal or biliary colic, post-operative pain, gout and arthritis. In addition, the injectable composition of the invention may be used prophylactically to prevent the formation of prostaglandins during and after surgery, with subsequent reduction in immediate post-operative pain.

The injectable composition may also be used for veterinary purposes.

The injectable composition is suitable for intravenous or intramuscular injection. The injectable composition is also suitable for Y-site administration.

The following examples relate to the preparation of inclusion complexes between I or II and III, their characterization, and pharmaceutical compositions containing them.

The buffers mentioned in the examples correspond to Sorenson's sodium phosphate buffer (Flynn, G. L. (1980) J. Parent. Drug Ass. 34(2), 139–162) and the European Pharmacopoeia potassium phosphate buffer.

EXAMPLE 1

The solubilizing effect of III on II may be directly demonstrated by solubility isotherms (performed according to Higuchi, T. & Connors, K. A. (1965) Adv. Anal. Chem. Instr. 4, 117) shown in FIG. 1. Briefly, to an excess of II, varying concentrations of III in solutions of either $NaH_2PO_4$ at pH 6.0 or deionized water acidified to pH 5.0 with 0.1N HCl were added. The mixtures were allowed to shake for 24 hours at room temperature and equilibrated for a further 24 hours. Samples were filtered through a 0.22 μm filter and analyzed U.V. spectrophotometrically for II. The basis for the increased aqueous solubility is the formation of an inclusion complex between the host (III) and guest (I or II). From the initial slope of the solubility isotherms, a 1:1 stoichiometric ratio may be assumed. The stability of the inclusion complex in solution may be improved by favouring the unionized form (i.e. I), although greater solubility of the complex is achieved above pH 6.0 particularly in the absence of buffer at pH 7.7. Values in parenthesis reflect the final pH at equilibrium.

EXAMPLE 2

A 1:1 solid complex of II/III is prepared by initially dissolving 7.50 g III in 10 ml deionized water at 35° C. To this solution 1.68 g II is added batchwise with vigorous stirring. The solution is stirred for a further 10–15 minutes and allowed to cool. The solution remains clear. Lyophilization provides an amorphous white solid containing about 180 mg II per gram of the complex as determined by HPLC. The complex is readily soluble in water.

Figure 2:
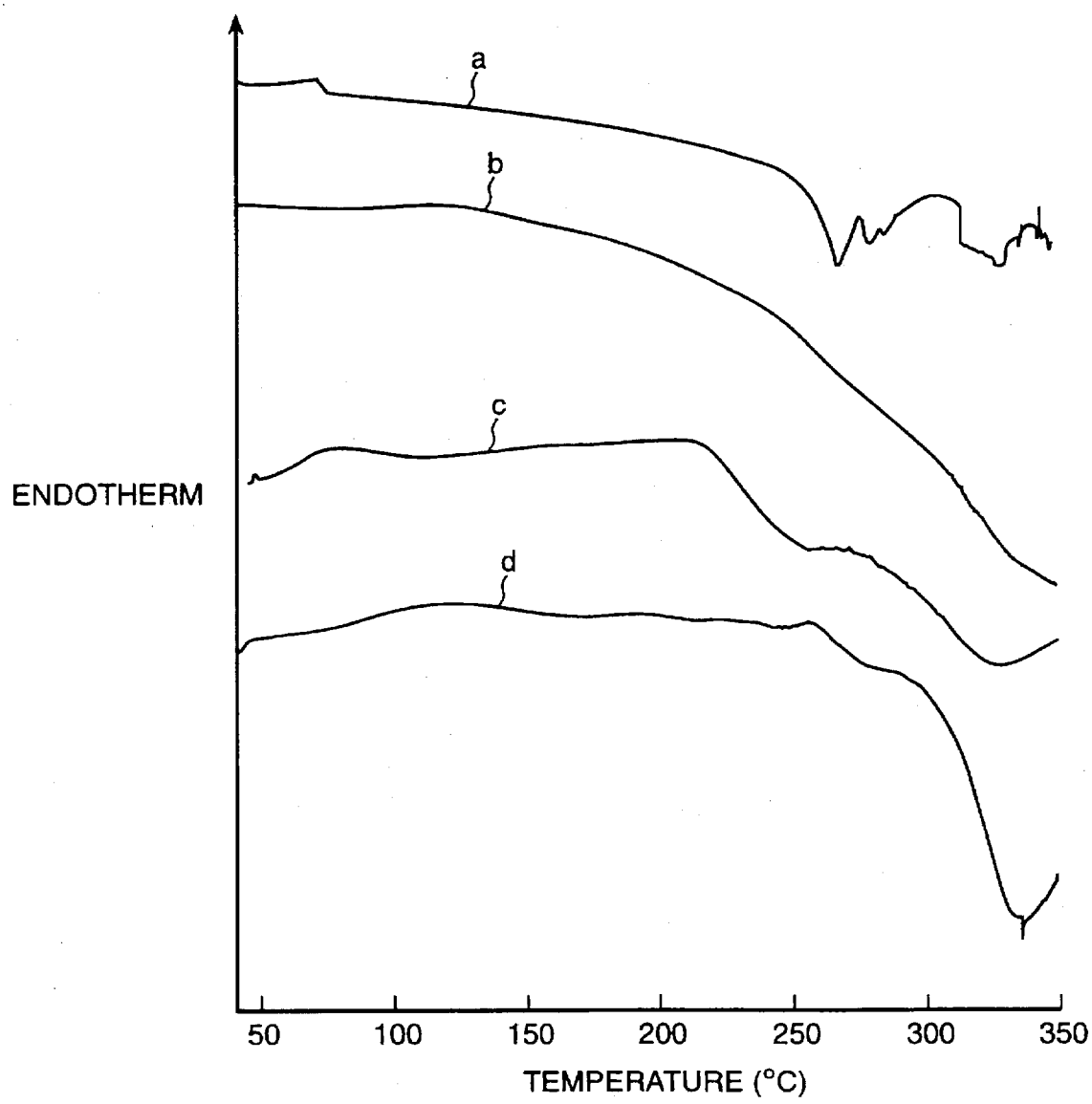
FIG. 2 is a DSC thermal analysis of diclofenac sodium and 2-hydroxypropyl beta-cyclodextrin.

Evidence for solid state complex formation is obtained by DSC analysis from the absence of a thermal transition between 260° and 290° C., characteristic of II and physical mixtures of II and III as illustrated in FIG. 2 where a) is diclofenac sodium, b) is 2-hydroxypropyl beta-cyclodextrin, c) is a physical mixture of a) and b), and d) is an inclusion complex of a) and b) formed in solution and lyophilized. Curves were recorded on a Perkin-Elmer DSC 7 instrument heating at 10° C. per minute.

Figure 3:
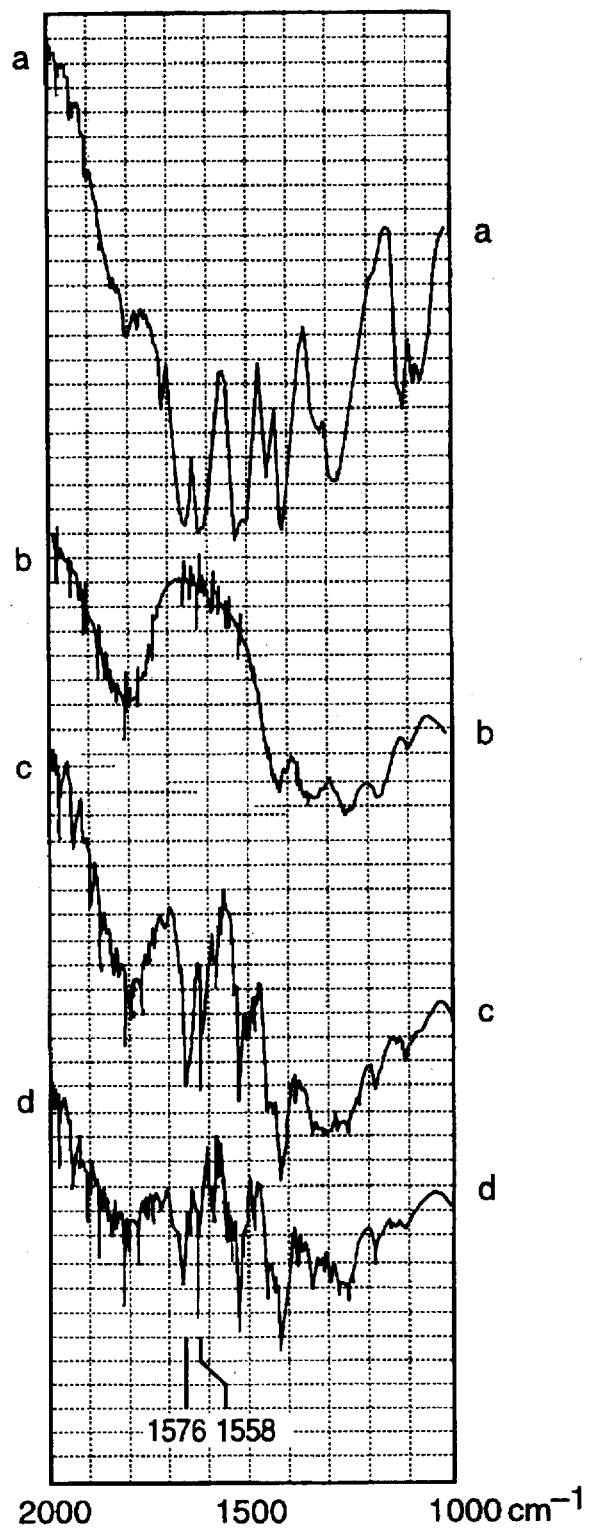
FIG. 3 is an FTIR analysis of diclofenac sodium and hydroxypropyl beta-cyclodextrin.

The solid complex is further characterized by IR spectra recorded from potassium bromide discs. The spectra shown in FIG. 3 reveal a decrease in the intensity of the carboxylate C=O bands at 1558 and 1576 cm$^{-1}$ of the complex relative to spectra of II and physical mixtures of II and III. This pattern may be attributed to intermolecular interaction between the carboxyl group of II and hydroxyl functionalities of the cyclodextrin as a consequence of complexation (Lin, S-Z., Wouessidjewe, D., Poelman, M-C., Duchêne, D., 1991, Int. J. Pharm. 69, 211–219).

The inclusion complex formed between II and III in aqueous solution is directly demonstrable from proton magnetic resonance spectra described below.

Characterization of Inclusion Complexation in Aqueous Solution by Proton Magnetic Resonance.

Figure 4A:
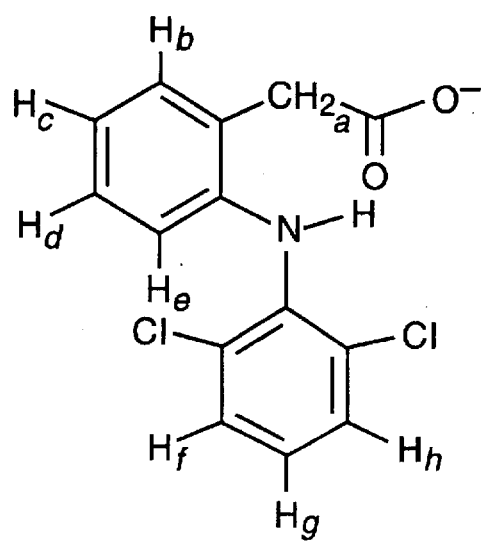
FIG. 4 illustrates the structures and notation used in the description of the NMR data.
Figure 4B:
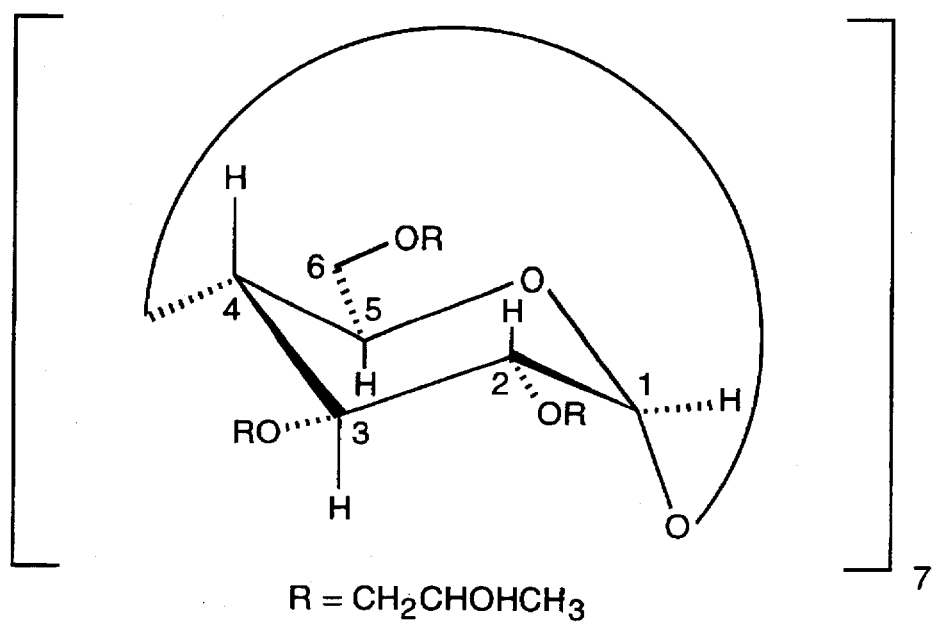

Pure 20 mg samples of II, III, and the lyophilized complex, prepared as described in Example 2, were each dissolved in $D_2O$ (0.5 ml). Proton magnetic resonance experiments were performed using a Bruker AMX 500 NMR spectrometer with probe temperature controlled at 303K. The structures and proton notation of II and III are given in FIG. 4.

Unambiguous resonance assignments of II could be made from multiplicity of signals and two dimensional correlation spectroscopy. Owing to the heterogeneous composition of III, unambiguous assignment of all protons was not possible. Nevertheless, the anomeric ($C_1$) and 2-hydroxypropyl protons were assigned based on chemical shift and signal intensity. The resonances of other protons were assigned based on correspondence with experimental values for unsubstituted β-cyclodextrin.

Figure 6A:
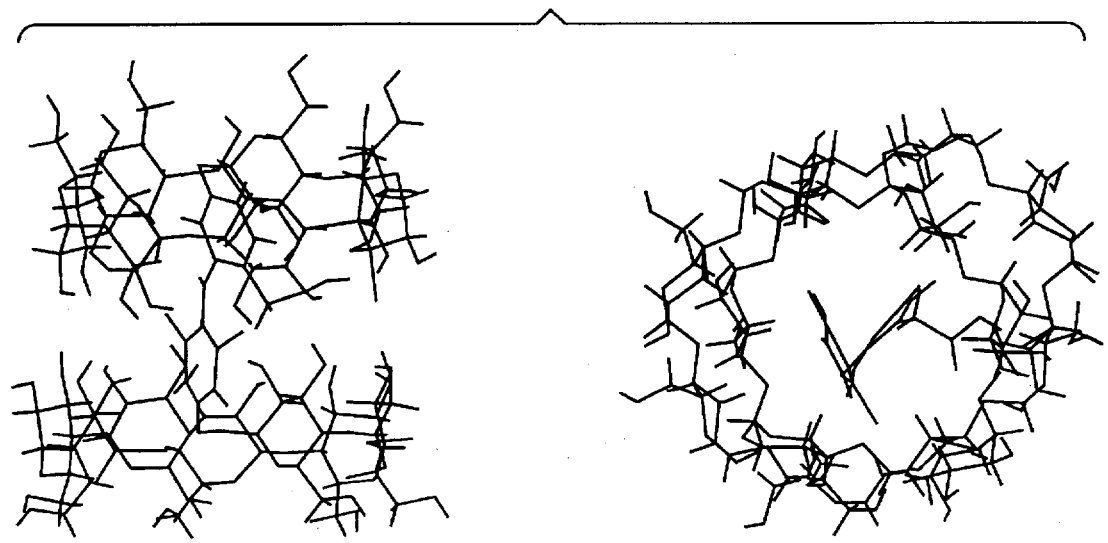
FIG. 6a is a proton magnetic resonance based molecular model of the aqueous inclusion complex formed between diclofenac and hydroxypropyl beta-cyclodextrin, with two perspective views being shown and with the diclofenac being shown in bold and the hydroxypropyl groups omitted for clarity.
Figure 6B:
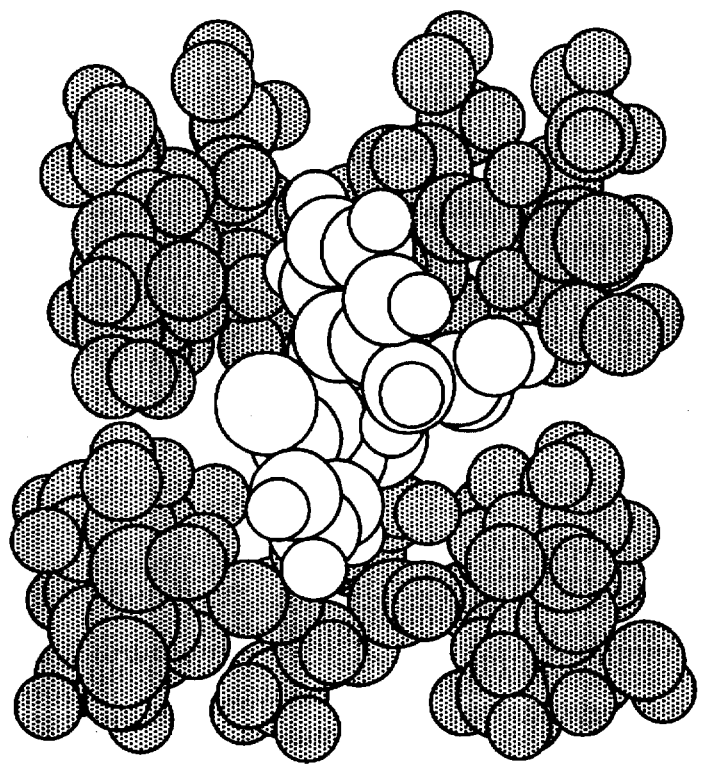
FIG. 6b is a space filling model of FIG. 6a, with the Z-axis being partially cut away to reveal the interaction between the aromatic rings of diclofenac and the hydrophobic cyclodextrin cavity.

It is well known that the 3 and 5 protons of beta cyclodextrins are oriented towards the centre of the cavity, whereas the 1, 2, 4 and 6 protons are oriented outside the cavity. Molecular inclusion may be directly demonstrated by distance dependant magnetization transfer between guest protons and the 3, 5 cyclodextrin protons. A two dimensional rotating frame overhauser enhancement spectroscopy (ROESY) spectrum of the complex reveals through space coupling between the b, d, e, f, g and h protons of II and the 3, 5 protons of III as shown in FIG. 5. The same experiment was performed using a 1:1.5 mol/mol lyophilized complex of II and unsubstituted β-cyclodextrin which gave a similar result and confirmed cross peak assignments for the 3,5 protons which in this case were more clearly resolved multiplets. The intensity of the cross peaks is related to the intermolecular interproton distance and thus the nature of the inclusion interaction may be modeled as shown in FIGS. 6a and 6b. It is evident that both aromatic rings are capable of inclusion despite the presence of a 1:1 mol/mol ratio of II:III.

The result suggests that a 1:2 molar ratio II:III may favour simultaneous inclusion of both aromatic rings in aqueous solution. Further evidence for interaction of both aromatic rings of II with the internally oriented 3 and 5 protons of III was obtained from significant shifts of protons e, f and h ranging from 0.027 to 0.052 ppm relative to values for pure II, whereas the other aromatic protons experience shifts of less than 0.010 ppm.

EXAMPLE 3

Water (350 ml), purified by reverse osmosis, is adjusted to pH 5 with 0.1N HCl and heated to 35° C. 2-Hydroxypropyl β-cyclodextrin with a degree of substitution (DS) of 4.7 (75.00 g) is added with stirring. The solution is stirred for 5 minutes and diclofenac sodium (12.50 g) is slowly added with vigorous stirring. The solution is stirred for 30 minutes at 35° C. A sample is removed, allowed to cool and the osmolarity measured. If necessary, sorbitol (in an amount calculated to bring the osmolality of the solution at final volume of 500 ml to between 280–300 mOsm/l) is slowly added with stirring. The heat is removed and stirring is continued until room temperature is reached. Final volume adjustment is made with water and the solution is stirred for 15 minutes. The pH at equilibrium is 7.4±0.4. The solution is optionally first filtered through a 0.45 micron filter and deoxygenated with nitrogen or deoxygenated and finally passed through 0.22 micron membrane filter into presterilized amber ampoules under nitrogen atmosphere and aseptic conditions. The ampoules are sealed under nitrogen. The solution contains 25,0±0,8 mg/ml diclofenac sodium as determined by validated HPLC.

EXAMPLE 4

Water (500 ml), purified by reverse osmosis, is adjusted to pH 4.5 with 0.1N HCl. A 350 ml portion of the acidified water is heated to 35° C. and 2-hydroxypropyl-β-cyclodextrin D.S. 4.69 (102 g) is added with stirring. The solution is stirred for 5 minutes and diclofenac sodium (12.50 g) is slowly added with vigorous stirring. The solution is stirred for 30 minutes at 35° C. The heat is removed and stirring is continued until room temperature is reached. The volume is adjusted to 500 ml with the remainder of the acidified water and the solution is stirred for 15 minutes. The pH at equilibrium is 7.4±0.6. The solution is deoxygenated with nitrogen and passed through 0.22 micron membrane filter into presterilized amber ampoules under nitrogen atmosphere and aseptic conditions. The fill volume of the ampoules is 3.3 ml. The ampoules are sealed under nitrogen. The solution contains 25.0±0.7 mg/ml diclofenac sodium as determined by validated HPLC. The osmolarity of the solution corresponds to between 280 and 320 mOsm/kg. Ampoules stored for 12 weeks at 45° C. and 12 months at room temperature (20°–25° C.) respectively show no visible signs of crystallization or significant deviation in pH and osmolarity and contain 100%±5% original diclofenac content as determined by stability indicating HPLC with the absence of any degradation compounds as evidenced using diode array detection.

EXAMPLE 5

A double blind cross-over randomised study to compare the relative bioavailability of diclofenac sodium 75 mg/3 ml formulated with 2-hydroxypropyl-beta-cyclodextrin (HPB) according to Example 3 administered intramuscularly (i.m.) and intravenously (i.v.), with a reference product diclofenac sodium 75 mg/3 ml commercial injection administered i.m., was conducted in six human volunteers [FARMOVS 19/94, Institute for Clinical Pharmacology and Drug Development, University of the Orange Free State, Bloemfontein, South Africa]. The main pharmacokinetic data obtained in the said study is presented in Table 1. The plasma diclofenac concentration versus time curves for diclofenac sodium-HPB (i.v. and i.m.) and commercial diclofenac sodium (i.m.) are shown in FIG. 7.

TABLE 1

Summary of the comparative pharmacokinetic results: Geometric mean (SD)

| Product | Dose* (mg) | $C_{max}$ (ng/ml) | $T_{max}$ (h) (median) | $t_{1/2}^z$(h) | AUC (ng.h/ml) |
|---|---|---|---|---|---|
| Commercial diclofenac sodium (i.m.) | 75 | 1682(1.26) | 0.50 | 1.52(1.21) | 3861 (1.13) |
| Diclofenac sodium-HPB (i.m.) | 75 | 2761(1.39) | 0.50 | 0.76(1.22) | 3698 (1.09) |
| Diclofenac sodium-HPB (i.v.) | 75 | 12828(1.40) | 0.08 | 0.73(1.46) | 3852 (1.15) |

*Corresponding to diclofenac sodium

The pharmacokinetics results indicate that the two products are bioequivalent with respect to diclofenac absorbed after i.m. administration. However, diclofenac sodium-HPB reached higher maximum concentrations ($C_{max}$) in a shorter time ($t_{1/2}^z$) than commercial diclofenac sodium i.m. The absolute bioavailability of diclofenac sodium-HPB i.m. is close to 100% when compared to diclofenac sodium-HPB i.v. No clinically significant adverse effects or changes in clinical chemistry were observed during the study, except for a slight, albeit reversible increase in serum aspartate aminotransferase activity that was noted in 2/6 subjects at the end of the treatment period. Both subjects received commercial diclofenac sodium i.v. as last dose. It is therefore very probable that this finding was related to local reactions produced by the intramuscular injections applied in the cross-over design, rather than to an effect of diclofenac sodium-HPB. Preparations of diclofenac according to the invention may thus be effectively used by either i.m. or i.v. routes of administration.

We claim:

1. A method of preparing an injectable pharmaceutical or veterinary composition comprising diclofenac as an active ingredient wherein the diclofenac active ingredient consists essentially of either (a) a pharmaceutically acceptable salt of diclofenac and 2-hydroxypropyl beta-cyclodextrin, or (b) an inclusion complex of a pharmaceutically acceptable salt of diclofenac and 2-hydroxypropyl beta-cyclodextrin, or a mixture of (a) and (b), having a molar ratio of pharmaceutically acceptable salt of diclofenac to 2-hydroxypropyl beta-cyclodextrin from 1:1 to 1:10 which includes the step of:

(i) dissolving either (a) a pharmaceutically acceptable salt of diclofenac and 2-hydroxypropyl beta-cyclodextrin, or (b) an inclusion complex of a pharmaceutically acceptable salt of diclofenac and 2-hydroxypropyl beta-cyclodextrin, or a mixture of (a) and (b), in water to form a solution, the water having been acidified to a pH such that the pH of the solution is from 6.0 to 8.5 inclusive, wherein dissolution of either (a) or (b) is carried out in the absence of a buffer that causes crystallization of the diclofenac salt out of solution.

2. The method according to claim 1 wherein the diclofenac active ingredient consists essentially of (a) and the molar ratio of the pharmaceutically acceptable salt of diclofenac to 2-hydroxypropyl beta-cyclodextrin is from 1:1.5 to 1:2.5.

3. The method according to claim 1 wherein the diclofenac active ingredient consists essentially of (b) and the molar ratio of the pharmaceutically salt of diclofenac to 2-hydroxypropyl beta-cyclodextrin is from 1:1.5 to 1:2.5.

4. The method according to claim 3 wherein the diclofenac active ingredient consists essentially of (b) and the complex is prepared by mixing together with kneading or grinding an amount of the pharmaceutically acceptable salt of diclofenac and an amount of 2-hydroxypropyl beta-cyclodextrin.

5. The method according to claim 1 wherein the average degree of substitution of the 2-hydroxypropyl beta-cyclodextrin is between 3.9 and 5.1 inclusive 2-hydroxypropyl groups per cyclodextrin molecule.

6. The method according to claims 1 wherein the solution has a concentration of diclofenac of 10 mg per milliliter or more.

7. An injectable pharmaceutical or veterinary composition comprising diclofenac as an active ingredient wherein the diclofenac active ingredient consists essentially of either (a) a pharmaceutically acceptable salt of diclofenac and 2-hydroxypropyl beta-cyclodextrin, or (b) an inclusion complex of a pharmaceutically acceptable salt of diclofenac and 2-hydroxypropyl beta-cyclodextrin, or a mixture of (a) and (b), having a molar ratio of pharmaceutically acceptable salt of diclofenac to 2-hydroxypropyl beta-cyclodextrin from 1:1 to 1:10 in an aqueous vehicle in the form of a solution or for reconstitution with an aqueous vehicle to give a solution, the solution having a pH of from 6.0 to 8.5 inclusive, the solution being free of a buffer that causes crystallization of the diclofenac salt out of solution.

8. The composition according to claim 7 wherein the diclofenac active ingredient consists essentially of (a) and the molar ratio of the pharmaceutically acceptable salt of diclofenac to 2-hydroxypropyl beta-cyclodextrin is from 1:1.5 to 1:2.5.

9. The composition according to claim 7 wherein the diclofenac active ingredient consists essentially of (b) and the molar ratio of the pharmaceutically acceptable salt of diclofenac to 2-hydroxypropyl beta-cyclodextrin is from 1:1.5 to 1:2.5.

10. The composition according to claim 7 wherein the average degree of substitution of the 2-hydroxypropyl beta-cyclodextrin is between 3.9 and 5.1 inclusive 2-hydroxypropyl groups per cyclodextrin molecule.

11. The composition according to claim 7 wherein the composition has a concentration of diclofenac of 10 mg per milliliter or more.

12. The composition according to claim 11 wherein the composition has a concentration of diclofenac of about 25 mg per milliliter.

13. The composition according to claim 7 formulated in unit dose form, each unit dose containing from 10 mg to 150 mg inclusive of diclofenac.

* * * * *